United States Patent

Rao

[11] Patent Number: 5,824,270
[45] Date of Patent: Oct. 20, 1998

[54] ON-LINE WATER MONITOR

[76] Inventor: Tenneti V. Rao, 128 W. Pleasant St., Apt. #G1, Manlius, N.Y. 13104

[21] Appl. No.: 895,078

[22] Filed: Jul. 16, 1997

Related U.S. Application Data

[63] Continuation of Ser. No. 515,301, Aug. 15, 1995, abandoned.

[51] Int. Cl.[6] ..................................................... G11N 21/27
[52] U.S. Cl. ....................... 422/82.09; 422/62; 422/82.05
[58] Field of Search .................... 422/62, 82.05, 422/82.09; 436/73–84, 50, 51; 210/739, 745, 143

[56] References Cited

U.S. PATENT DOCUMENTS

| | | | |
|---|---|---|---|
| 5,030,419 | 7/1991 | Ellis et al. | 422/82.09 |
| 5,126,272 | 6/1992 | Kingston, Jr. et al. | 436/77 |
| 5,128,068 | 7/1992 | Lahoda et al. | 252/626 |
| 5,414,195 | 5/1995 | Peterson et al. | 422/50 |
| 5,459,276 | 10/1995 | Kuhn et al. | 436/74 |
| 5,464,587 | 11/1995 | Lippitsch et al. | 422/82.07 |
| 5,545,517 | 8/1996 | Thompson et al. | 436/73 |

OTHER PUBLICATIONS

Willard et al., Instrumental Methods of Analysis; Wadsworth Publishing Co., Belmont, CA; 1981; p. 496.

*Primary Examiner*—Jill Warden
*Attorney, Agent, or Firm*—Trapani & Molldrem

[57] ABSTRACT

An ultra high sensitive on-line water monitor is disclosed. The on-line water monitor can determine the concentration of a wide range of inorganic contaminants in water at parts per trillion level in real time. The list of inorganic elements detectable by the instrument is as follows: Be, Mg, Ca, Th, V, Ti, Cr, W, Mn, Fe, Co, Ni, Cu, Au, Zn, Cd, Al, Pb, Sb, Bi, Hg, and other elements which are suitable for detection and assaying with spectrophotometric (also known as colorimetric) technique. The on-line water monitor described herein surpasses the currently available analytical instruments (such as inductively coupled mass spectrometers (ICP-MS), atomic absorption spectrometers, and atomic emission spectrometers) in a number of factors: cost, on-line operation, speed, ease of automation, low power requirements, sensitivity, and selectivity. The instrument will have a wide range of applications in the fields of environmental monitoring, environmental remediation, drinking water purification, water recycling, industrial processes, pharmaceutical industry, space vehicles, and space stations.

13 Claims, 4 Drawing Sheets

FIG.3

| OPTICS: SOURCE, DETECTOR, OPTICAL ELEMENTS, CHOPPER |

| ELECTRONICS: SIGNAL CONDITIONING, AMPLIFIERS, POWER SUPPLY, PROCESS CONTROLLING, OUTPUT SIGNALS |

| SOFTWARE: ROUTINES FOR SELF-CHECK, CALIBRATION, CONCENTRATION MEASUREMENT, DATA STORAGE, AND DATA COMMUNICATION |

| FLUIDICS: MIXING, FILTRATION, METERED FLOW |

| CHEMISTRY: MASKING AGENTS, ORGANIC CHELATING REAGENTS, SOLVENTS, STABILITY CONSTANTS, REACTION TIME (EQUILIBRIUM). |

ON-LINE WATER MONITOR

This application is a continuation of application Ser. No. 08/515,301, filed Aug. 15, 1995, now abandoned.

REFERENCES CITED

1. Disclosure document no. 341350 by T.V. Rao.
2. J. A. Cotruvo, "EPA policies to protect the health of consumers of Drinking Water in the United States," in 'Water Supply and Health', edited by H. van Lelyveld and B. C. J. Zoeteman, Elsevier, New York 1981, p. 348.
3. USEPA, Proposed Rule (Aug. 18, 1988- Federal Register).
4. "Trace element analysis by computer aided stripping potentiometry," by A. M. Graabaek and B. Jeberg, American Laboratory, May 1993, p. 27.
5. "ICP-MS instrumentation," by C. Tye and P. Hitchen, American Laboratory, 2(1992), p. 20.
6. E. B. Sandell and H. Onishi, Photometric Determination of Traces of Metals, John Wiley, New York, 1978.
7. T. G. Nolan and N. J. Dovichi, Ultrasensitive Analysis with the Crossed Beam Thermal Lens, IEEE Circuits Devices Mag., 2, 54, 1986.
8. N. J. Dovichi, CRC Critical Reviews in Analytical Chemistry, 17, 357, 1986.
9. "True Blue," by E. Corcoran, Scientific American, September 1991, p. 171.
10. K. Burger, "Organic Reagents in Metal Analysis," Pergamon, 1973, New York.
11. Z. Marczenko, CRC Critical Reviews in Anal. Chem. 11 (1981) p. 195.
12. Technical literature on gas and diode pumped solid state lasers, Coherent Inc., Santa Clara, Calif.

SUMMARY

A novel instrument for trace element analysis is the subject of invention described in reference 1. Conventionally inorganic impurities or contaminants in water are determined by analyzing the water sample with the aid of atomic emission spectroscopy, atomic absorption spectroscopy, or mass spectrometry (ref. 2). Recently a few additional techniques such as ion selective electrode and computerized stripping potentiometry (ref. 4) have also come into practice. Most of the analytical instruments still suffer from a number of disadvantages such as high cost, complexity, large power requirements, cumbersome size, off-line operation, and the need for a skilled operator.

A comparison of the various analytical techniques and their limits of detection is given in table I. It is possible that through continuous refinements both the cost and quality (ref. 5) of traditional analytical equipments (such as inductively coupled plasma mass spectrometers (ICP-MS)) may improve with time. However, such conventional analytical instruments are extremely complex to adapt as on-line techniques in the field or at the point of source; also as of now they are heavily dependent on human operator for sampling and loading. The on-line water monitor as described here surpasses all the currently available instruments in a number of factors: cost, range of inorganic elements (Be, Mg, Ca, Th, V, Ti, Cr, W, Mn, Fe, Co, Ni, Cu, Au, Zn, Cd, Al, Pb, Sb, Bi, Hg, and many others), speed, automation, low power requirements, sensitivity, on-line operation, and selectivity. Also, the lowest detectable concentration is at least several orders of magnitude less than the proposed Environmental Protection Agency (EPA) (ref. 3) maximum contaminant level for inorganics.

Being modular in design, with a few component changes and tuning, the instrument can be modified to detect a wide range of inorganic contaminants. Most importantly, it can automatically sample the water, determine the impurity concentration, and store the data. Periodically, it can check itself for proper functioning, self-calibrate, and give warning signals about malfunctioning. Self-calibration is accomplished by sending a standard solution (known as spiking) of a given contaminant (ex: 0.1 ppb lead solution) through the on-line water monitor and comparing the measured Pb concentration with the known value, i.e., 0.1 ppb. Microprocessor based instrument systems are well amenable to self-testing tasks. Such design concepts are well known to skilled persons in the art of test and analytical instrumentation.

PRINCIPLE OF OPERATION

Two fundamental principles are utilized in the operation of the instrument. The Lambert-Beer law states:

$$A = a.b.c$$

where
 a is absorptivity, A is absorbance
 b is the optical beam path length in cm and
 c is the concentration of the absorbing species, in moles/liter.

Therefore, measuring A is equivalent to measuring c, if a and b are known. Values of a, i.e., absorptivities for a large number of metal complexes are available in published scientific literature. b is an instrumental parameter.

The second principle is the measurement of very low absorbances. This is possible with laser optic measurements. The lowest value of measurable absorbance in conventional spectrophotometers (non-laser type) is only 0.001; this yields 0.02 ppm (parts per million) as the lowest detectable limit for lead with the complexing agent dithizone. In laser experiments, absorbance measurements as low as $10^{-7}$ are routinely performed (see references 7, 8). This implies that lead levels as low as 2 ppt (parts per trillion) are measurable with laser spectrophotometric experimental arrangement using the complexing agent dithizone. The details of such a laser spectrophotometric technique are described in the following sections.

In the present instrument, the metal-organic reagent complex in an organic (or aqueous) medium is placed in a small precision cuvette made of glass or quartz. As an example, the case of lead contaminant in water is considered. The Pb-dithizonate complex is dissolved in an organic solvent. The complex formation of dithizone with lead is highly selective and the only interfering ions are Sn, Pd, and Au (ref. 10). Such interferences can be eliminated by the use of a masking agent (chemical reagent). A pump laser beam illuminates the sample and produces a highly localized rise in temperature (FIG. 4). The temperature increase is often very small (<1° C.) but finite and such a thermal disturbance produces refractive index changes in the liquid medium. The pump laser creates spatially and temporally (i.e., in time) an active thermal lens. A sensing laser beam in a crossed direction can probe the thermal lens and obtain accurate physical information about the liquid. The physical information includes absorbance, refractive index, and variation of refractive index with temperature.

FIG. 3 illustrates the modular concept of design. The design makes it easy to tune, i.e., selectively detect a particular inorganic element. For example, lead detection is performed with dithizone reagent. To determine the concentration of chromium, the reagent will be replaced by another, such as 1,5-diphenyl carbazide. Simultaneous detection of several contaminants is also possible by using several cuvettes. The laser beam can be rotated to probe each cuvette sequentially. Alternatively, the cuvettes can be placed on a turntable and each cuvette can be exposed to the laser beam sequentially. However, the latter arrangement will need proper arrangements to turn-on/off fluid paths without leaks or spillage.

BRIEF DESCRIPTION OF THE DRAWINGS

FIG. 3 is a modular representation of the device.

DETAILED DESCRIPTION

Figure 1:
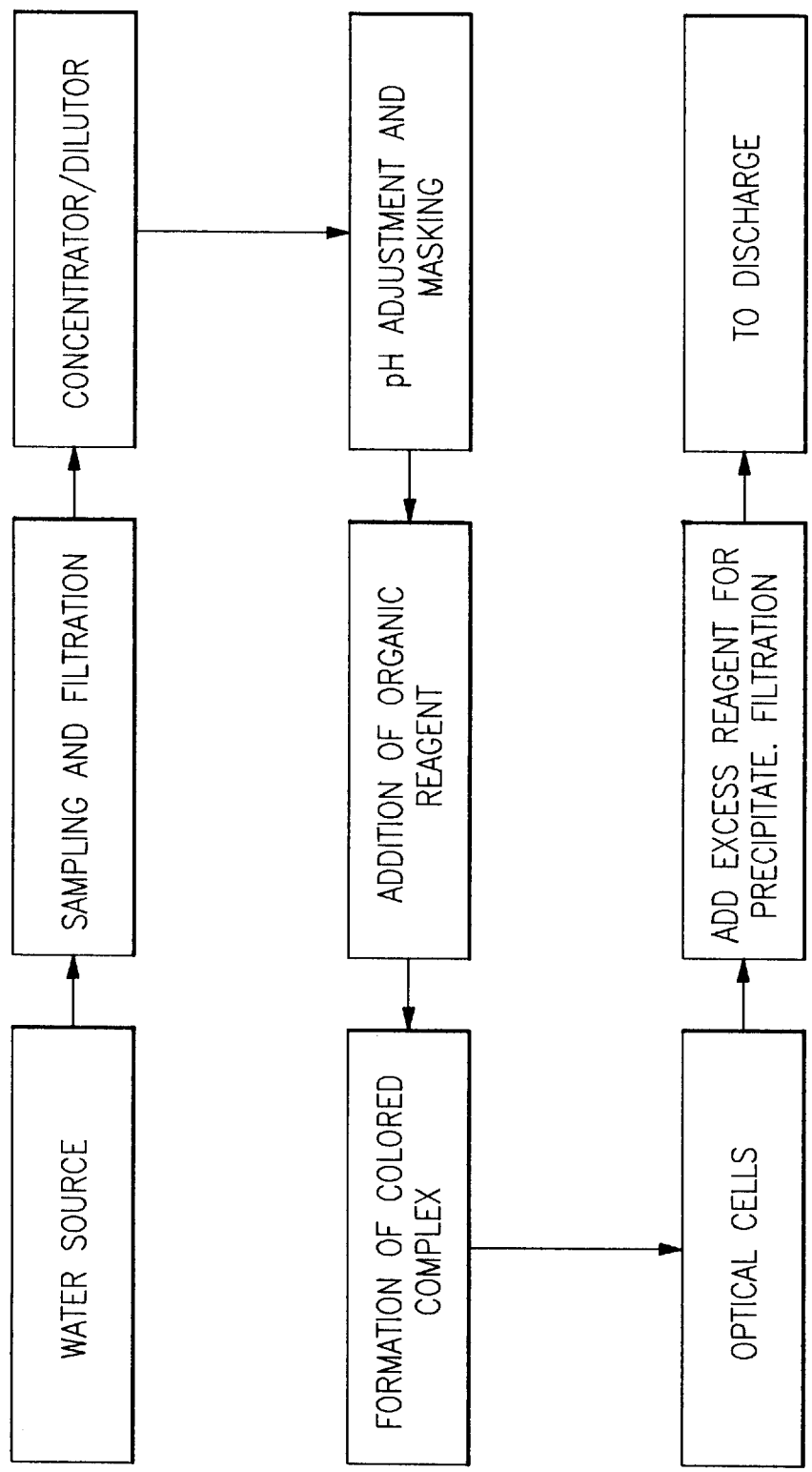
FIG. 1 is a schematic of the invention.

The functioning of the instrument is described with the aid of FIGS. 1–4. FIG. 1 depicts the basic scheme of the operation of the analytical instrument. Water from a source is pumped into the instrument and filtered to remove particulate matter. After appropriate dilution (if needed) the pH of water is adjusted. In some instances, instead of dilution, the incoming water is subjected to concentration. If necessary, a masking agent is added to eliminate the effect of interfering ions. After masking, a small amount of highly selective and sensitive organic complexing agent is added to the solution to form a colored a complex. The absorbance of the colored solution is measured to determine the concentration of inorganic contaminant or impurity. Under the control and supervision of a microprocessor system, the whole sequence of events repeats continuously to generate concentration versus time data.

Figure 2:
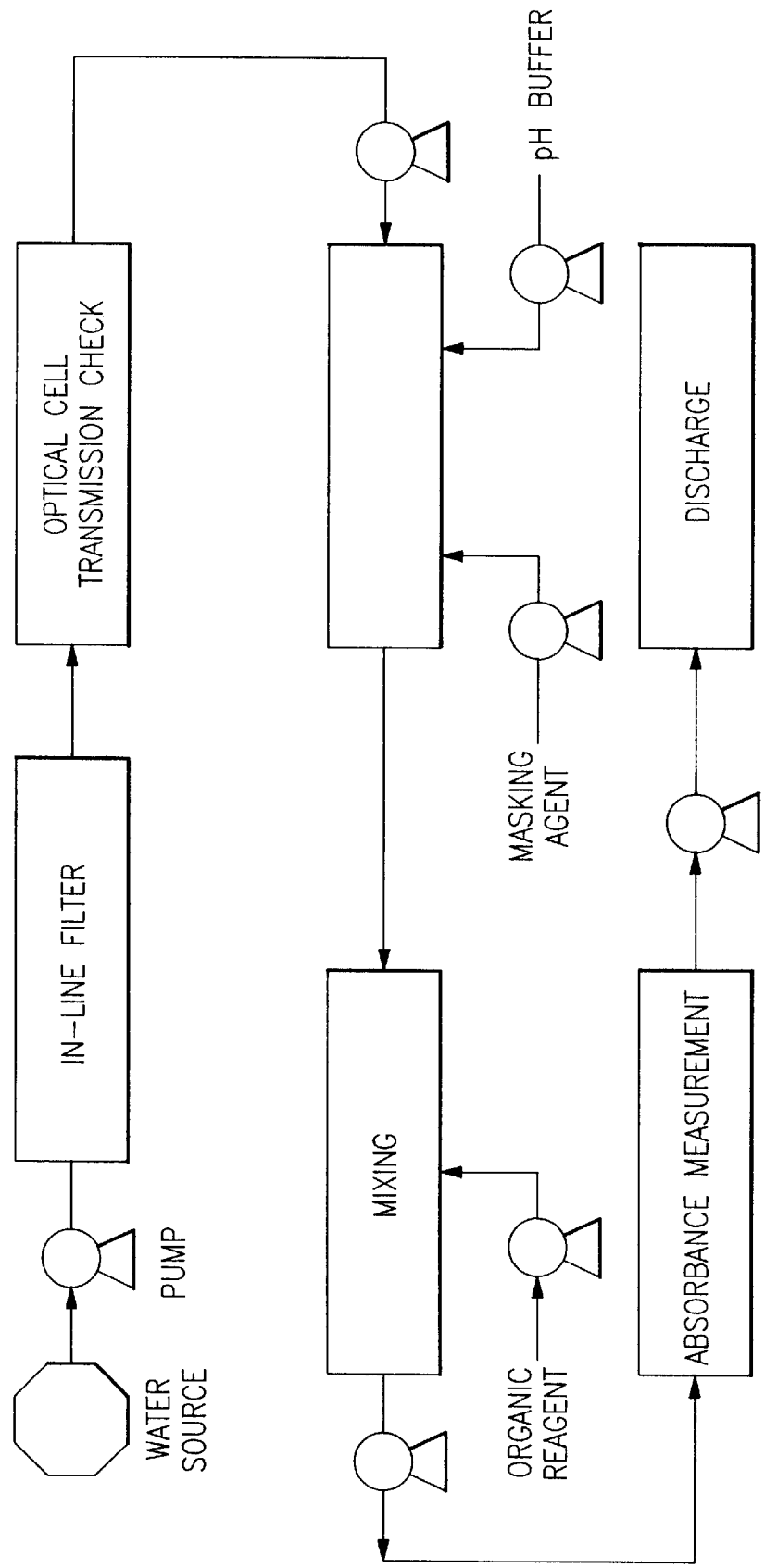
FIG. 2 is a schematic of the flow path of the device.

FIG. 2 illustrates the path of fluid from the source to discharge. Electronically controlled pumps (similar to the ones used in liquid and gas chromatographs) and other fluid transfer and controlling devices (such as pipettes and burettes) are utilized to make the entire instrument automatic. Only small amounts (sometimes as low as a few microliters) of water is required for a single measurement. After absorbance measurement, the analyzed water can be collected as waste water. Or after measurement, the water can be processed in-situ and clean water can be discharged into the source (ex: lake, stream, etc.)

In FIG. 3 the total instrumentation operation is subdivided into several parts. Such a design makes it easy to construct the on-line water monitor in a modular form. A set of absorptivities for a large number of inorganic colored complexes are permanently stored in the memory. Also, instrumental parameters like optical path length are stored in the memory. Change of contaminant (say from Pb to Cr) can be accomplished by changing the complexing agent, the pH, masking, and other experimental conditions. Such changes can be activated by the microprocessor or manually by a human operator.

Figure 4:
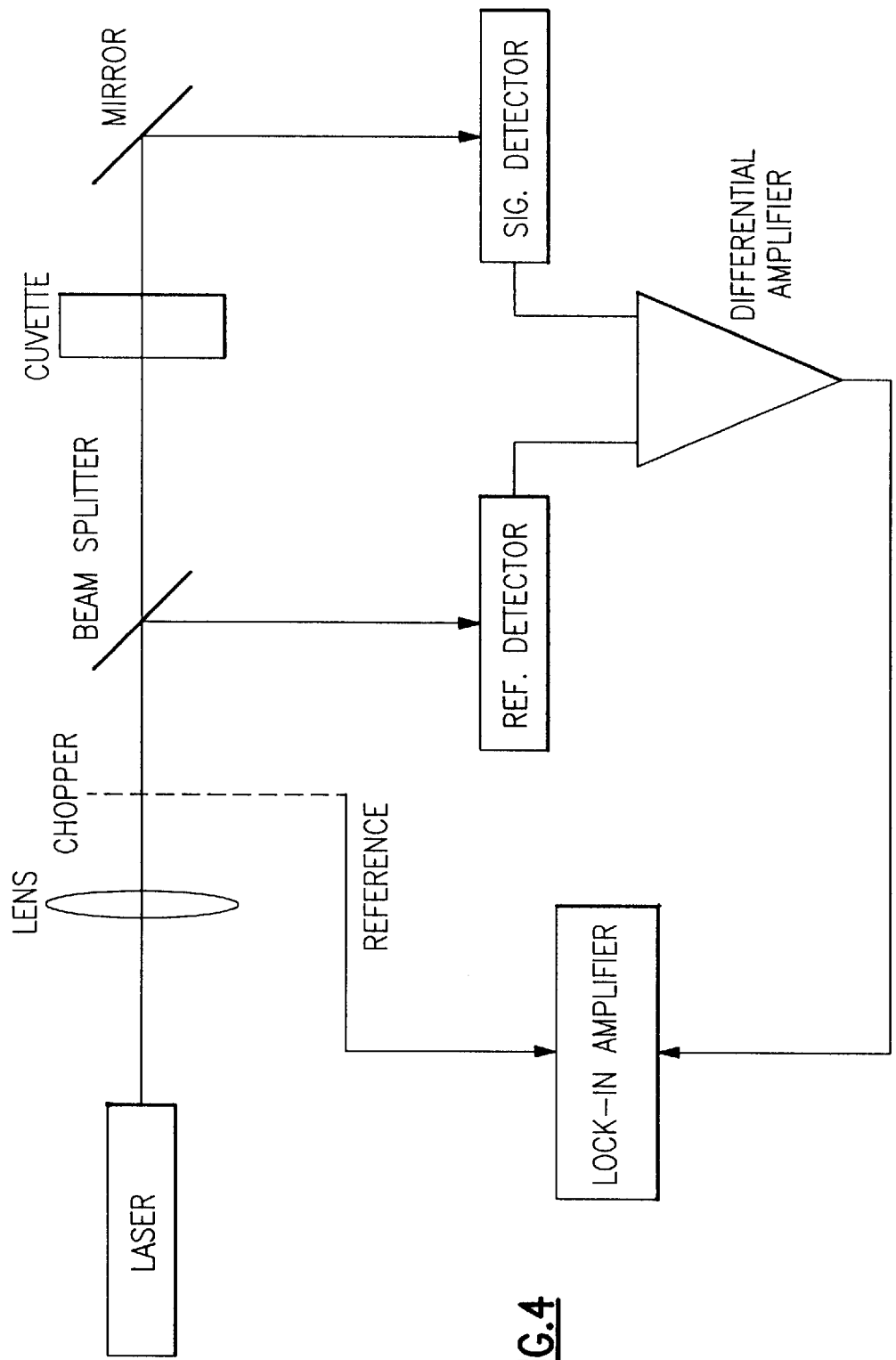
FIG. 4 is a simplified laser optic device for use in the invention.

FIG. 4 is the heart of absorbance measurement. The laser beam from a laser source is chopped and split into two beams: one for the colored liquid sample held in cuvette and the other for the reference. Beam chopping can be accomplished by either pulsing the laser or electroptically or mechanically with a rotating shutter. Experimentally the single beam lock-in amplifier technique was found suitable to measure absorbances as low as $~10^{-7}$. For a cobalt-PAN system, such an experimental setup (ref. 8) produced a detection limit of $2 \times 10^{-7}$M.

One of the key components in the proposed instrument is a compact laser source. Several new portable, compact lasers in the visible region (0.4–0.7 micron wavelength) are available commercially and these are described in references 9 and 12. Some of the other salient features of the invention are as follows: the analytical instrument can be installed at remote locations and can be left unattended. The data (i.e., contaminant concentration versus clock time) can be transmitted via telephone cable or through radio waves or a combination of both. The data can be transmitted to a central office for further data processing. Alternatively, the data can be transmitted to a cellular telephone network and then passed onto a central data processing station.

The instrument can be operated aboard a marine vehicle to assess the quality of water in rivers, sea, and streams. During the periods of floods, it provides a speedy and accurate way of monitoring the water quality. In times of heavy rains and floods, the river/stream waters get contaminated with a number of sources such as sewage discharge, runaway water from landfills and other waste lands. Similar contamination of water resources also occurs due to hazardous chemical accidents. The on-line water helps in such instances to monitor the quality of water, analyze the contaminants, and measure them. The instrument can be installed at sewage treatment facilities to measure inorganic contaminants before they are discharged into creeks, lakes, or rivers. When placed at the entrance of sewage treatment facility, the monitor will keep a close record of the pollutants coming from the upstream. The on-line water monitor can be used at a number of industrial sites (such as plating and chemical plants) to determine the level of inorganics going into effluents and help to take corrective actions in real time. This will help the industries and public organizations to faithfully comply with the EPA (Environmental Protection Agency) guidelines.

The instrument will benefit the following industries in the monitoring of water quality: water works authorities, consumers' points-of-use, mineral water and beverages bottling plants, semiconductor fabrication plants, chemical plants, and pharmaceutical manufacturers. It is possible that a person well versed in the art of instrumentation and analytical chemistry may find other suitable applications or modify the on-line water monitor to fit his/her needs. Although the details of such usage are not specifically given here, the disclosure is in sufficient detail to help future developments.

A number of improvements and modifications of the basic design can be incorporated to enhance the performance of the instrument. The instrument can operate with rechargeable batteries for several weeks without operator assistance. The batteries can be powered with a solar cell panel. The total power requirements will depend on the frequency of sampling, data storage, and communication demands. A large number of organic complexing agents with varying specificity and sensitivity are available commercially; a list of organic reagents is given in reference 10.

TABLE I

Detection Limits in Solution - a Comparison

| | | |
|---|---|---|
| Flame emission | 200 ng/ml | 16 ppb |
| Atomic absorption | 10 ng/ml | 0.8 ppb |
| Ion selective electrode (Orion Pb ISE) | | 0.2 ppm |
| Spectrophotometry with 1 cm cell | | 0.02–0.002 ppm |
| Fe-1,10-phenanthroline thermal lens experiment. | $6 \times 10^{-8}$ g/l (120 atoms) | <5 ppt |

TABLE I-continued

Detection Limits in Solution - a Comparison

| | | |
|---|---|---|
| Computerized stripping potentiometry - Pb | | 0–20 ppb |
| ICP-MS for lead | | >0.5 ppb |
| Safe Drinking Water Act 1988 (ex: Pb)* | <0.005 mg/l | <0.0004 ppm |

*Note: This is not an instrument.

I claim that:

1. An on-line instrument for measuring an impurity in a water source, comprising:

(a) intake means for receiving, on-line, a water sample from the water source;

(b) means for mixing a reagent with the water sample such that a selective color complex is formed from a reaction with the reagent and the impurity in the water sample;

(c) processing means, in direct fluid communication with said intake means and said mixing means, for processing the water sample prior to mixing in said mixing, means, said processing means consisting essentially of:
      (i) filter means for removing particulate matter from said water sample,
      (ii) means for introducing a chemical masking agent to the water sample, such that other impurities in the water sample are masked and substantially prevented from interfering with the selective color complex produced by said mixing means,
      (iii) means for adjusting the pH of the water sample,
      (iv) means for adjusting the concentration of the impurity in the water sample, and
      (v) means for checking the transmittance of the water sample;

(d) means, including a spectrophotometric cell in fluid communication with said mixing means, for measuring the absorbance of the selective color complex in the cell by way of a laser spectrophotometric technique;

(e) discharge means for draining the selective color complex from the spectrophotometric cell after the absorbance measurement is made, whereby a flow-through path for the water sample is defined from said intake means to said discharge means; and (f) control means, operatively coupled to said flow-through path, for controlling the on-line operation of said instrument.

2. The on-line instrument of claim 1, wherein said absorbance measurement means includes:

(i) a laser source which produces a laser beam;
   (ii) means, operatively coupled to said laser source, for chopping said laser beam and creating a first reference signal therefrom;
   (iii) means for splitting the laser beam into a reference beam and a sensing beam, the sensing beam being directed through the selective color complex contained in the spectrophotometric cell and altered by the selective color complex;
   (iv) first photo-detection means, optically coupled to the reference beam, for detecting the reference beam and producing a second reference signal therefrom;
   (v) second photo-detection means, optically coupled to the sensing beam downstream of said spectrophotometric cell, for detecting the altered sensing beam and producing a sensing signal therefrom;
   (vi) a differential amplifier, coupled to said first and second photo-detection means, for generating a differential signal which is proportional to the difference between the sensing signal and the second reference signal; and
   (vii) a lock-in amplifier, coupled to said differential amplifier for generating an absorbance signal from the differential signal and the first reference signal, the absorbance of the selective color complex being determined from said absorbance signal.

3. The on-line instrument of claim 1, wherein the impurity to be measured by said on-line instrument is an inorganic impurity.

4. An on-line instrument for measuring an impurity in a water source, comprising:

(a) intake means for receiving, on-line, a water sample from the water source;

(b) means for mixing a reagent with the water sample such that a selective color complex is formed from a reaction with the reagent and the impurity in the water sample;

(c) processing means, in direct fluid communication with said intake means and said mixing means, for processing the water sample prior to mixing in said mixing means, said processing means consisting essentially of:
      (i) filter means for removing particulate matter from said water sample,
      (ii) means for introducing a chemical masking agent to the water sample, such that other impurities in the water sample are masked and substantially prevented from interfering with the selective color complex produced by said mixing means,
      (iii) means for adjusting the pH of the water sample, and
      (iv) means for adjusting the concentration of the impurity in the water sample;

(d) means, including a spectrophotometric cell in fluid communication with said mixing means, for measuring the absorbance of the selective color complex in the cell by way of a laser spectrophotometric technique;

(e) discharge means for draining the selective color complex from the spectrophotometric cell after the absorbance measurement is made, whereby a flow-through path for the water sample is defined from said intake means to said discharge means; and (f) control means, operatively coupled to said flow-through path, for controlling the on-line operation of said instrument.

5. An on-line instrument for measuring an impurity in a water source, comprising:

(a) intake means for receiving, on-line, a water sample from the water source;

(b) means for mixing a reagent with the water sample such that a selective color complex is formed from a reaction with the reagent and the impurity in the water sample;

(c) processing means, in direct fluid communication with said intake means and said mixing means, for processing the water sample prior to mixing in said mixing means, said processing means consisting essentially of:
      (i) filter means for removing particulate matter from said water sample,
      (ii) means for introducing a chemical masking agent to the water sample, such that other impurities in the water sample are masked and substantially prevented from interfering with the selective color complex produced by said mixing means,
      (iii) means for adjusting the pH of the water sample, and (iv) means for checking the transmittance of the water sample;

(d) means, including a spectrophotometric cell in fluid communication with said mixing means, for measuring the absorbance of the selective color complex in the cell by way of a laser spectrophotometric technique;

(e) discharge means for draining the selective color complex from the spectrophotometric cell after the absorbance measurement is made, whereby a flow-through path for the water sample is defined from said intake means to said discharge means; and (f) control means, operatively coupled to said flow-through path, for controlling the on-line operation of said instrument.

6. An on-line instrument for measuring an impurity in a water source, comprising:

(a) intake means for receiving, on-line, a water sample from the water source;

(b) means for mixing a reagent with the water sample such that a selective color complex is formed from a reaction with the reagent and the impurity in the water sample;

(c) processing means, in direct fluid communication with said intake means and said mixing means, for processing the water sample prior to mixing in said mixing means, said processing means consisting essentially of:
  (i) filter means for removing particulate matter from said water sample,
  (ii) means for adjusting the pH of the water sample, and
  (iii) means for checking the transmittance of the water sample;

(d) means, including a spectrophotometric cell in fluid communication with said mixing means, for measuring the absorbance of the selective color complex in the cell by way of a laser spectrophotometric technique;

(e) discharge means for draining the selective color complex from the spectrophotometric cell after the absorbance measurement is made, whereby a flow-through path for the water sample is defined from said intake means to said discharge means; and (f) control means, operatively coupled to said flow-through path, for controlling the on-line operation of said instrument.

7. An on-line instrument for measuring an impurity in a water source, comprising:

(a) intake means for receiving, on-line, a water sample from the water source;

(b) means for mixing a reagent with the water sample such that a selective color complex is formed from a reaction with the reagent and the impurity in the water sample;

(c) processing means, in direct fluid communication with said intake means and said mixing means, for processing the water sample prior to mixing in said mixing means, said processing means consisting essentially of:
  (i) means for introducing a chemical masking agent to the water sample, such that other impurities in the water sample are masked and substantially prevented from interfering with the selective color complex produced by said mixing means,
  (ii) means for adjusting the pH of the water sample,
  (iii) means for adjusting the concentration of the impurity in the water sample, and
  (iv) means for checking the transmittance of the water sample;

(d) means, including a spectrophotometric cell in fluid communication with said mixing means, for measuring the absorbance of the selective color complex in the cell by way of a laser spectrophotometric technique;

(e) discharge means for draining the selective color complex from the spectrophotometric cell after the absorbance measurement is made, whereby a flow-through path for the water sample is defined from said intake means to said discharge means; and (f) control means, operatively coupled to said flow-through path, for controlling the on-line operation of said instrument.

8. An on-line instrument for measuring an impurity in a water source, comprising:

(a) intake means for receiving, on-line, a water sample from the water source;

(b) means for mixing a reagent with the water sample such that a selective color complex is formed from a reaction with the reagent and the impurity in the water sample;

(c) processing means, in direct fluid communication with said intake means and said mixing means, for processing the water sample prior to mixing in said mixing means, said processing means consisting essentially of:
  (i) means for introducing a chemical masking agent to the water sample, such that other impurities in the water sample are masked and substantially prevented from interfering with the selective color complex produced by said mixing means,
  (ii) means for adjusting the pH of the water sample, and
  (iii) means for adjusting the concentration of the impurity in the water sample;

(d) means, including a spectrophotometric cell in fluid communication with said mixing means, for measuring the absorbance of the selective color complex in the cell by way of a laser spectrophotometric technique;

(e) discharge means for draining the selective color complex from the spectrophotometric cell after the absorbance measurement is made, whereby a flow-through path for the water sample is defined from said intake means to said discharge means; and (f) control means, operatively coupled to said flow-through path, for controlling the on-line operation of said instrument.

9. An on-line instrument for measuring an impurity in a water source, comprising:

(a) intake means for receiving, on-line, a water sample from the water source;

(b) means for mixing a reagent with the water sample such that a selective color complex is formed from a reaction with the reagent and the impurity in the water sample;

(c) processing means, in direct fluid communication with said intake means and said mixing means, for processing the water sample prior to mixing in said mixing means, said processing means consisting essentially of:
  (i) filter means for removing particulate matter from said water sample, and
  (ii) means for checking the transmittance of the water sample;

(d) means, including a spectrophotometric cell in fluid communication with said mixing means, for measuring the absorbance of the selective color complex in the cell by way of a laser spectrophotometric technique;

(e) discharge means for draining the selective color complex from the spectrophotometric cell after the absorbance measurement is made, whereby a flow-through path for the water sample is defined from said intake means to said discharge means; and (f) control means, operatively coupled to said flow-through path, for controlling the on-line operation of said instrument.

10. An on-line instrument for measuring an impurity in a water source, comprising:
   (a) intake means for receiving, on-line, a water sample from the water source;
   (b) means for mixing a reagent with the water sample such that a selective color complex is formed from a reaction with the reagent and the impurity in the water sample;
   (c) processing means, in direct fluid communication with said intake means and said mixing means, for processing the water sample prior to mixing in said mixing means, said processing means consisting essentially of:
      (i) means for introducing a chemical masking agent to the water sample, such that other impurities in the water sample are masked and substantially prevented from interfering with the selective color complex produced by said mixing means, and
      (ii) means for adjusting the pH of the water sample;
   (d) means, including a spectrophotometric cell in fluid communication with said mixing means, for measuring the absorbance of the selective color complex in the cell by way of a laser spectrophotometric technique;
   (e) discharge means for draining the selective color complex from the spectrophotometric cell after the absorbance measurement is made, whereby a flow-through path for the water sample is defined from said intake means to said discharge means; and
   (f) control means, operatively coupled to said flow-through path, for controlling the on-line operation of said instrument.

11. An on-line instrument for measuring an impurity in a water source, comprising:
   (a) intake means for receiving, on-line, a water sample from the water source;
   (b) means for mixing a reagent with the water sample such that a selective color complex is formed from a reaction with the reagent and the impurity in the water sample;
   (c) processing means, in direct fluid communication with said intake means and said mixing means, for processing the water sample prior to mixing in said mixing means, said processing means consisting essentially of:
      (i) means for adjusting the pH of the water sample, and
      (ii) means for adjusting the concentration of the impurity in the water sample;
   (d) means, including a spectrophotometric cell in fluid communication with said mixing means, for measuring the absorbance of the selective color complex in the cell by way of a laser spectrophotometric technique;
   (e) discharge means for draining the selective color complex from the spectrophotometric cell after the absorbance measurement is made, whereby a flow-through path for the water sample is defined from said intake means to said discharge means; and
   (f) control means, operatively coupled to said flow-through path, for controlling the on-line operation of said instrument.

12. An on-line instrument for measuring an impurity in a water source, comprising:
   (a) intake means for receiving, on-line, a water sample from the water source;
   (b) means for mixing a reagent with the water sample such that a selective color complex is formed from a reaction with the reagent and the impurity in the water sample;
   (c) processing means, in direct fluid communication with said intake means and said mixing means, for processing the water sample prior to mixing in said mixing means, said processing means consisting essentially of:
      (i) means for adjusting the pH of the water sample, and
      (ii) means for checking the transmittance of the water sample;
   (d) means, including a spectrophotometric cell in fluid communication with said mixing means, for measuring the absorbance of the selective color complex in the cell by way of a laser spectrophotometric technique;
   (e) discharge means for draining the selective color complex from the spectrophotometric cell after the absorbance measurement is made, whereby a flow-through path for the water sample is defined from said intake means to said discharge means; and
   (f) control means, operatively coupled to said flow-through path, for controlling the on-line operation of said instrument.

13. An on-line instrument for measuring an impurity in a water source, comprising:
   (a) intake means for receiving, on-line, a water sample from the water source;
   (b) means for mixing a reagent with the water sample such that a selective color complex is formed from a reaction with the reagent and the impurity in the water sample;
   (c) processing means, in direct fluid communication with said intake means and said mixing means, for processing the water sample prior to mixing in said mixing means, said processing means consisting essentially of means for adjusting the pH of the water sample;
   (d) means, including a spectrophotometric cell in fluid communication with said mixing means, for measuring the absorbance of the selective color complex in the cell by way of a laser spectrophotometric technique;
   (e) discharge means for draining the selective color complex from the spectrophotometric cell after the absorbance measurement is made, whereby a flow-through path for the water sample is defined from said intake means to said discharge means; and
   (f) control means, operatively coupled to said flow-through path, for controlling the on-line operation of said instrument.

* * * * *